United States Patent [19]

Steppe et al.

[11] Patent Number: 4,787,889
[45] Date of Patent: Nov. 29, 1988

[54] RIGID, TRANSPARENT FLUID CONDUIT FOR SURGICAL IRRIGATION

[75] Inventors: Dennis L. Steppe, Tustin; Stephen W. Haines, Santa Ana, both of Calif.

[73] Assignee: CooperVision, Inc., Menlo Park, Calif.

[21] Appl. No.: 119,268

[22] Filed: Nov. 9, 1987

Related U.S. Application Data

[63] Continuation of Ser. No. 780,813, Sep. 27, 1985, abandoned.

[51] Int. Cl.⁴ .............................................. A61B 17/20
[52] U.S. Cl. ........................................ 604/22; 604/27; 604/35; 604/264; 128/305
[58] Field of Search .............................. 604/22, 27–35, 604/43, 264; 128/305

[56] References Cited

U.S. PATENT DOCUMENTS

| | | | |
|---|---|---|---|
| 3,306,291 | 2/1967 | Burke | 604/110 |
| 3,589,363 | 6/1971 | Banko | 604/28 |
| 3,865,113 | 2/1975 | Sharon et al. | 128/305 |
| 4,316,465 | 2/1982 | Dotson, Jr. | 128/305 |
| 4,386,927 | 6/1983 | Eichenbaum | 604/51 |
| 4,465,470 | 8/1984 | Kelman | 604/28 |
| 4,515,583 | 5/1985 | Sorich | 604/22 |
| 4,516,398 | 5/1985 | Wuchinich | 604/22 |
| 4,526,571 | 7/1985 | Wuchinich | 604/22 |

Primary Examiner—C. Fred Rosenbaum
Assistant Examiner—Mario Costantino
Attorney, Agent, or Firm—Vorys, Sater, Seymour and Pease

[57] ABSTRACT

An improved irrigation fluid conduit for use with a coaxial surgical irrigator-aspirator for ophthalmic surgery comprises a hollow body adapted for attachment to the surgical irrigator-aspirator and a thin-walled tubular sleeve extending from the hollow body to surround the aspiration conduit of the instrument. The body and sleeve are homogeneously molded from polypropylene, which permits a rigid thin wall sleeve having a wall thickness not greater than 0.006 inches and which is transparent for increased visibility of the adjacent tissues.

27 Claims, 2 Drawing Sheets

RIGID, TRANSPARENT FLUID CONDUIT FOR SURGICAL IRRIGATION

This is a continuation of prior application Ser. No. 780,813, filed on Sept. 27, 1985 entitled Rigid, Transparent Fluid Conduit for Surgical Irrigation now abandoned.

BACKGROUND OF THE INVENTION

1. Field of the Invention

This invention relates to molded plastic fluid conduits and more particularly to thin-walled, rigid, transparent fluid conduits suitable for use in surgical irrigation-aspiration apparatus.

2. Description of the Prior Art

In performing delicate surgical procedures within the anterior chamber of the eye, it is necessary to make at least one penetrating incision passing through the peripheral tissues of the eye such as the cornea, the sclera, and the like. A particularly common procedure is the removal of a cataract by ultrasonic fragmentation and aspiration through a small-diameter ultrasonically vibrated needle having an axial aspiration conduit, which is inserted through an incision just large enough to accomodate the diameter of the tool. Fluid leakage though the incision as well as removal of aqueous humor by aspiration through the ultrasonic needle leads to loss of the aqueous humor from the interior of the eye. If this fluid is not replaced, the anterior chamber of the eye will collapse, with serious consequences for the health of the eye, particularly for the delicate corneal endothelium. Accordingly, in order to prevent this collapse it is conventional to provide a supply of irrigating fluid to the interior of the eye, either through a secondary incision in the eye or by means adapted for both irrigation and aspiration through a single incision. The single incision method is generally preferred, but it requires an irrigation-aspiration apparatus having a double lumen tube with the separate channels for irrigation and aspiration placed either side by side or coaxially. The coaxial configuration has certain advantages, especially for ultrasonic surgical instruments having provision for irrigations and aspiration. Such an instrument which incorporates an ultrasonic fragmenting and aspirating needle and a coaxial irrigation conduit is disclosed, e.g., in Banko and Kelman, U.S. Pat. No. 3,589,363.

The performance requirements of a sleeve which defines the irrigating channel in a coaxial surgical irrigator/aspirator place severe demands on the materials and design of the sleeve. The sleeve should have a low heat conductivity to insulate the tissue at the sides of the incision from heat generated by friction with the ultrasonic tool. It should be sufficiently strong to prevent collapse under pressure from the sides of the incision. At the same time it should be as of a small diameter as possible to allow a minimum size incision. It is also helpful if the sleeve is transparent to provide better visibility for the surgeon. Finally, because the element is small and of rather precise dimensions, it is desirable that it be capable of being formed by molding for economical manufacture.

The materials hitherto used in the fabrication of such irrigation sleeves have each had certain drawbacks. Metal sleeves, e.g., stainless steel, have the advantage of rigidity, which makes them easier to insert through a small incision and less likely to injure the ocular tissues such as the corneal endothelial cell layer and Descemet's membrane. Since they cannot be collapsed by pressure from the sides of the incision, they make it easier to assure a constant flow rate of irrigation fluid. However, because of their extreme rigidity, they must be very precisely matched to the shape of the interior aspiration conduit, so that many different sleeves are needed to accomodate various aspiration conduits. Furthermore, because of their heat conductivity, they do not protect the adjacent tissues from heat generated when the aspiration conduit is an ultrasonically vibrated surgical tool. Accordingly, metal sleeves have hitherto not been used with ultrasonic surgical instruments but only with simple irrigation-aspiration devices.

Synthetic resins, in the cross-sections required for irrigation sleeves, tend to be lacking in rigidity and/or strength. This requires a larger incision, either to accommodate a larger wall thickness or to minimize the force from the sides of the incision which tends to collapse the sleeve. Furthermore, some plastics are not transparent, and, like metal sleeves, obscure the surgeon's vision. U.S. Pat. No. 3,589,363 recommends the use of a sleeve of polytetrafluoroethylene, which is inert, but difficult to fabricate and is not perfectly transparent, even in thin sections. A commonly used commercial irrigation sleeve is made from silicone rubber and is molded integrally with a cap for fastening the sleeve to the ultrasonic handpiece. Silicone rubber can be conveniently molded by injection molding, but is flexible and tends to collapse under pressure from the incision and to fold back on itself or "telescope" when it is inserted through the incision. Furthermore, it is at best translucent, so that the surgeon's vision is somewhat obscured.

Hence a need has continued to exist for a surgical irrigation conduit which is free from the drawbacks of the known irrigation conduits.

SUMMARY OF THE INVENTION

It has now been found that an irrigation conduit having a sufficiently rigid wall with a wall thickness sufficiently small to be used as a sleeve in a coaxial surgical irrigation aspiration instrument and thereby to allow a conveniently small incision can be molded from certain polyolefin synthetic resins, particularly from polypropylene.

Accordingly, it is an object of this invention to provide a rigid irrigation or infusion sleeve which is easily inserted into a small incision.

A further object is to provide a rigid infusion sleeve which can be used generally with irrigation/aspiration handpieces with or without ultrasonic fragmentation.

A further object is to provide a rigid infusion sleeve which makes it easier to maintain fluidic balance through a small incision.

A further object is to provide a generally transparent infusion sleeve, which improves the visibility of the irrigation/aspiration or ultrasonic fragmenting tip and of the ocular structures during use.

A further object is to provide a rigid infusion sleeve which reduces the incidence of trauma to ocular tissues.

Further objects of the invention will become apparent from the description of the invention which follows.

DETAILED DESCRIPTION OF THE INVENTION AND PREFERRED EMBODIMENTS

Figure 1:
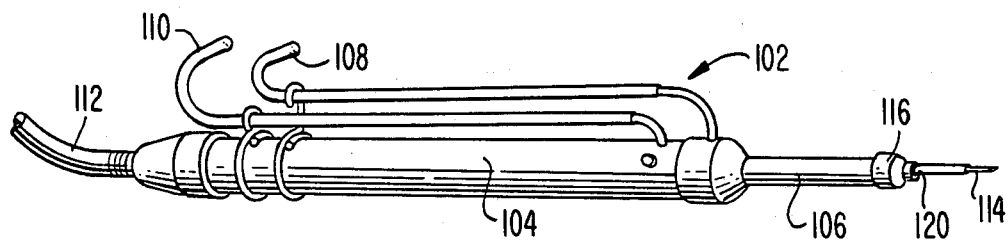
FIG. 1 shows an ultrasonic surgical irrigator-aspirator of the type which incorporates a tip cap/sleeve member which acts as an irrigation conduit.

The rigid infusion sleeve of this invention is designed to function as a part of a conventional ophthalmological surgical tool which incorporates coaxial irrigation and aspiration functions. An illustrative surgical instrument of this type wherein an elongated surgical tool or needle is ultrasonically vibrated to fragment tissue is depicted in FIG. 1. The surgical tool of this type comprises a handpiece 102 having a barrel 104 and an extension 106 which supports an ultrasonically vibrated surgical tool or needle 114. The handpiece is provided with a cable 112 containing power and control wires and cooling water tubes. The instrument is also provided with an aspiration line 110 which is connected to a source of vacuum and an irrigation line 108 connected to a source of irrigation fluid. Both lines are connected to passages within the handpiece leading to the region of the tip of the handpiece. The distal end of the handpiece is provided with an adaptor 116 and a tip cap and sleeve member 120 which surrounds the ultrasonic tool 114 and provides a coaxial annular passage for supplying irrigation fluid to the surgical site.

Figure 2:
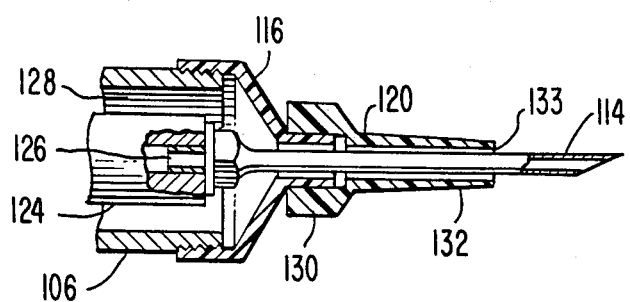
FIG. 2 shows a longitudinal section of the tip portion of the irrigator-aspirator of FIG. 1, showing the attachment of the tip cap and sleeve member to the handpiece.

FIG. 2 shows a detailed cross-section of the distal end of the handpiece 102. The ultrasonic tool 114 is fastened to the ultrasonically vibrating connecting member 124 by a threaded connection. An axial bore 126 in the ultrasonic tool communicates through conventional drilled passages in the ultrasonic connecting member 124 and the handpiece (not shown) with the aspiration line 110. The region between the ultrasonic connecting member 124 and the extension 106 provides a conduit 128 for irrigation fluid. This conduit is connected by conventional channels (not shown) in the handpiece 102 to the irrigation fluid line 108. The tip cap and sleeve member 120 fits on the end of the adapter 116, and is made up of a body member 130 and a sleeve member 132. The body member and sleeve member are preferably molded homogeneously from one synthetic resin material. The tip cap and sleeve member 120 surrounds the ultrasonic tool 114 to provide a coaxial fluid channel 133 which receives fluid from the fluid channel 128 and conducts it to the surgical site.

Figure 4:
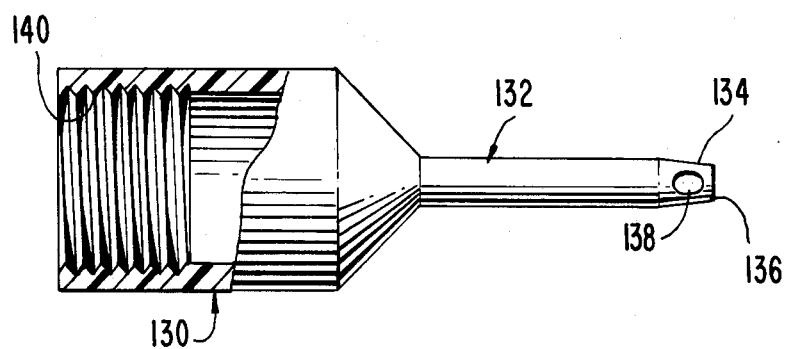
FIG. 4 shows a partial longitudinal section of a molded tip cap/sleeve of this invention.

The tip cap/sleeve 132 of this invention has a body portion 130 which is hollow and has means for engaging the front end of the surgical instrument so as to be in fluid communication with the passage or passages in the handpiece which supply irrigation fluid. The body portion of the tip cap and sleeve surrounds the ultrasonically vibrated needle and has an axis which is coincident with the axis of the ultrasonically vibrated needle. Generally, the body portion is cylindrical in shape and has a relatively thick wall provided with fastening means at one end of the body for engaging the end of the handpiece to be retained thereon. In the embodiment illustrated in FIG. 2, the means for engaging the end of the handpiece is simply the internal bore of the body member 130 which is press fit for the end of the adapter 116. Preferably, the fastening means are internal threads 140 on the wall of the body portion 130 (as shown in FIG. 4) which threadably engage external threads on the end of the handpiece to fasten the tip cap and sleeve thereto. The sleeve portion of the tip cap and sleeve of the invention is molded homogeneously with the body portion and is a tubular member having an axis coaxial with the axis of the body member and a wall thickness not greater than 0.006 inches. The cap and sleeve should be molded of a synthetic resin material which provides sufficient rigidity to prevent collapse under the pressure of the sides of the ocular incision, with accompanying decrease in irrigation and danger of excessive heating of the adjacent tissue. The synthetic resin used in the tip cap and sleeve should also be transparent so as not to obscure the surgeon's view of ocular structures, and preferably has a refractive index close to that of water, so that it becomes practically invisible when immersed in the aqueous humor of the eye, a property which enhances the surgeon's view of the surgical site. Polyolefin resins having sufficient rigidity to resist collapse are suitable materials for forming the fluid conduit of this invention. Such materials are obtainable in grades which are substantially transparent in thin wall sections and have a refractive index close to that of the aqueous humor and the irrigation fluid whereby they are substantially invisible in use and do not obstruct the surgeon's vision.

Figure 3:
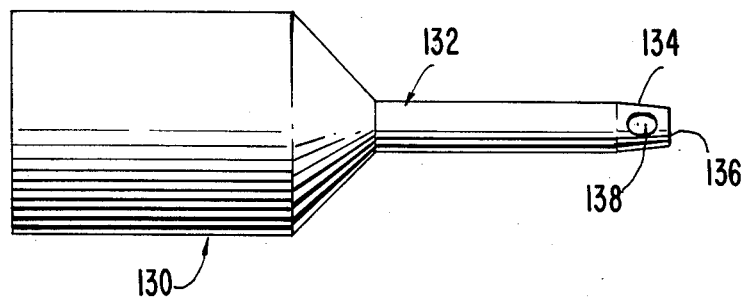
FIG. 3 shows a side elevation of a tip cap and sleeve member of this invention.

A preferred embodiment of the fluid conduit of this invention is shown in FIG. 3. The body member 130 and sleeve member 132 are molded homogeneously of one synthetic resin material. The radiused annulus distal tip 136 of the fluid conduit is sized to fit closely over the aspiration member of a surgical irrigator-aspirator and is provided with a tapered section 134 for easy insertion into the incision. Side infusion holes 138 are also formed in the sleeve member 132 to provide free flow of irrigation fluid to the surgical site.

FIG. 4 shows a partial section of the embodiment of FIG. 3 showing the internal threads 140 in the wall of the body member 130 which provide means for attaching the fluid conduit of the invention to the surgical irrigator-aspirator.

Figure 5:
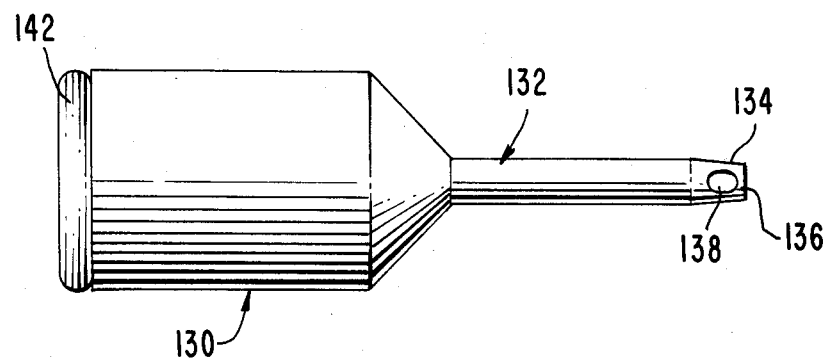
FIG. 5 shows a preferred embodiment of the fluid conduit of the invention incorporating an overmolded sealing ring.

FIG. 5 shows a preferred embodiment of the fluid conduit of the invention having a sealing ring 142 attached to the end of the body member 130. Preferably the sealing ring is made of a synthetic resin material selected for its sealing ability and is overmolded to form an integral part of the body member 130. A preferred material for the sealing ring is an elastomer, e.g., polyvinyl chloride.

While the illustrated surgical instrument is capable of ultrasonic tissue fragmentation, the invention is equally applicable to surgical instruments designed only for irrigation and aspiration.

A preferred material for the tip cap and sleeve of this invention is polypropylene. This material has the capability of being molded by injection molding in the thin wall sections which are required in the tip cap sleeve of this invention. It also has sufficient rigidity to prevent collapse of the sleeve under the normal compressive stress induced by contact with the sides of the incision. The material is also transparent and has a refractive index relatively close to that of the aqueous humor of the eye. Consequently, in use the sleeve is substantially invisible, and does not obstruct the surgeon's view.

The tip cap and sleeve of this invention is preferably made from polypropylene having a melt flow rate by ASTM D1238 of 9.0–12.0 grams/10 minutes, preferably 10.0–11.0 grams/10 min. The polypropylene preferably has a weight-average molecular weight, as measured by gel permeation chromatography, of about 220,000 to about 280,000, more preferably about 250,000.

The molding procedure for manufacturing the tip cap and sleeve of the invention is generally conventional but requires the usual care needed for molding thin sections in polypropylene. The mold is designed to be vented at the distal end of the irrigation sleeve core pin by means of a small vent machined into the mold to allow complete filling of the mold during injection of the molten resin. Preferably the mold is designed to provide for molding the ports at the distal end of the sleeve to eliminate a punching operation on the finished product. The completed molded unit is preferably flame treated on the distal end of the sleeve to remove any molding flash. The tip cap and sleeve of the invention may be molded in an injection molding machine of either the toggle clamp or hydraulic clamp type. In either case the mold-fill injection time should be about 8.0 seconds at a pressure of about 7000 psi. The injection time is somewhat critical in order to prevent material shearing and consequent burning of the material during mold-fill. After the injection phase, a part cooling cycle of about 11.0 seconds takes place, and the mold is then opened and the finished part is ejected. The nozzle temperature of the injection molding machine should be about 520°±20° F. for a toggle-clamp molding machine and about 500°±20° F. for a hydraulic clamp machine. In each case the clamp setting or clamp pressure should be backed off before the mold is filled to provide about 0.0008 inch parting line venting to assure complete filling of the mold during the material fill cycle.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. For use with an ophthalmological surgical instrument providing irrigating and aspirating functions, having an elongated handpiece containing an irrigation fluid supply conduit, and having an elongated tool connected to the handpiece, an irrigation fluid conduit comprising:

a hollow body portion including body walls surrounding an axis, a first end open for fluid transmissive communication with the irrigation fluid supply conduit, a second end having an axial opening therein, and an engaging means for engaging the handpiece;
   a tubular sleeve portion in fluid transmissive communication with said axial opening in said second end and coaxially extending therefrom, configured to surround the tool, and having a thin sleeve wall whose thickness is not greater than 0.006 inches;
   said hollow body portion and said tubular sleeve portion being homogeneously molded from a polyolefin synthetic resin which is transparent when immersed in the aqueous humour of the eye, so that, when in the eye, and the adjacent tissues can be visualized by the surgeon through said sleeve portion, and which resin is easy flowing to fully fill said thin sleeve wall, and which has a diametric rigidity great enough to prevent collapse of said sleeve portion when inserted into an ocular incision; and
   an elastomeric sealing ring overmolding said first end opening of said body section.

2. The conduit of claim 1 including,
   said polyolefin synthetic resin being polypropylene.

3. The conduit of claim 2 including
   said polypropylene having a melt flow index by ASTM D1238 of 9.0–12.0 grams/10 minutes.

4. The conduit of claim 3 including,
   said melt flow index being 10.0–11.0 grams/10 minutes.

5. The conduit of claim 2 including,
   said polypropylene having a molecular weight of about 220,000 to about 280,000.

6. The conduit of claim 5 including,
   said molecular weight being about 250,000.

7. The conduit of claim 2 including,
   said polypropylene having a melt flow index by ASTM D1238 of 10.0 to 11.0 grams/10 minutes and a molecular weight of about 250,000.

8. The conduit of claim 1 including,
   said wall thickness being not greater than 0.005 inches.

9. The conduit of claim 1 including,
   said engaging means including internal threads generally adjacent said open end of said body portion.

10. The conduit of claim 1 including,
    said body portion being generally cylindrical.

11. An ophthalmological surgical instrument providing irrigating and aspirating functions comprising:
    (A) an elongated handpiece;
    (B) an irrigation fluid supply conduit positioned in said handpiece;
    (C) an elongated tool connected to said handpiece; and
    (D) an irrigation fluid conduit comprising:
       a hollow body portion including body walls surrounding an axis, a first end open for fluid transmissive communication with said irrigation fluid supply conduit, a second end having an axial opening therein, and an engaging means for engaging said handpiece,
       a tubular sleeve portion in fluid transmissive communication with said axial opening in said second end and having a thin sleeve wall whose thickness is not greater than 0.006 inches,
       said hollow body portion and said tubular sleeve portion being homogeneously molded from a polyolefin synthetic resin which is transparent when immersed in the aqueous humor of the eye, so that said tool, when in the eye, and the adjacent tissues can be visualized by the surgeon through said sleeve portion, and which resin is easy flowing to fully fill said thin sleeve wall, and which has a diametric rigidity great enough to prevent collapse of said sleeve portion when inserted into an ocular incision, and
       an elastomeric sealing ring overmolding said first end opening of said body section.

12. The instrument of claim 11 including,
    said tool comprising a surgical aspiration tool.

13. The instrument of claim 12 including,
said surgical aspiration tool being ultrasonically vibrated surgical aspiration tool.
14. The instrument of claim 11 including,
said tool including an ultrasonically vibrated surgical needle.
15. The instrument of claim 11 including,
said tool having a tip, and
said sleeve portion having the distal end thereof having an internal radius large enough to provide for transition therethrough of said tip of said tool.
16. The instrument of claim 11 including,
said handpiece being generally cylindrical.
17. The instrument of claim 11 including,
an elongated tubular aspiration fluid supply conduit at one end of said handpiece.
18. The conduit of claim 11 including,
said polyolefin synthetic resin being polypropylene.
19. The conduit of claim 18 including,
said polypropylene having a melt flow index by ASTM D1238 of 9.0–12.0 grams/10 minutes.
20. The conduit of claim 19 including,
said melt flow index being 10.0–11.0 grams/10 minutes.
21. The conduit of claim 18 including,
said polypropylene having a molecular weight of about 220,000 to about 280,000.
22. The conduit of claim 21 including,
said molecular weight being about 250,000.
23. The conduit of claim 11 including,
said polypropylene having a melt flow index by ASTM D1238 of 10.0–11.0 grams/10 minutes and a molecular weight of about 250,000.
24. The conduit of claim 11 including,
said wall thickness being not greater than 0.005 inches.
25. The conduit of claim 11 including,
said engaging means including internal threads generally adjacent said open end of said body portion.
26. The conduit of claim 11 including,
said body portion being generally cylindrical.
27. For use with an ophthalmological surgical instrument providing irrigating and aspirating functions, having an elongated handpiece containing an irrigation fluid supply conduit, and having an ultrasonically-vibrated surgical needle connected to the handpiece, an irrigation fluid conduit comprising:

a hollow body portion including body walls surrounding an axis, a first end open for fluid transmissive communication with the irrigation fluid supply conduit, a second end having an axial opening therein, and an engaging means for engaging the handpiece;

a tubular sleeve portion in fluid transmissive communication with said axial opening in said second end and coaxially extending therefrom, configured to surround the needle, and having a thin sleeve wall whose thickness is not greater than 0.006 inches; and said hollow body portion and said tubular sleeve portion being homogeneously molded from a polyolefin synthetic resin which is transparent when immersed in the aqueous humor of the eye, so that, when said engaging means engages the handpiece, the needle, when in the eye, and the adjacent tissues can be visualized by the surgeon through said sleeve portion, and which resin is easy flowing to fully fill said thin sleeve wall, and which has a diametric rigidity great enough to prevent collapse of said sleeve portion when inserted into an ocular incision, and said polyolefin synthetic resin being polypropylene having a melt flow index by ASTM D1238 of 9.00 to 12.0 grams/10 minutes and a molecular weight of about 220,000 to about 280,000.

* * * * *